United States Patent [19]

Ishii et al.

[11] Patent Number: 4,526,623
[45] Date of Patent: Jul. 2, 1985

[54] METHOD OF CLEANING ENDOSCOPE CHANNELS

[75] Inventors: Fumiaki Ishii; Hiroyuki Sasa; Hisao Yabe; Yukio Nakajima; Koji Takamura; Takeaki Nakamura, all of Tokyo, Japan

[73] Assignee: Olympus Optical Co., Ltd., Tokyo, Japan

[21] Appl. No.: 599,707

[22] Filed: Apr. 11, 1984

[30] Foreign Application Priority Data

Apr. 15, 1983 [JP]  Japan .................................. 58-66799
Apr. 15, 1983 [JP]  Japan .................................. 58-66800
May 16, 1983 [JP]  Japan .................................. 58-85551

[51] Int. Cl.³ .......................... B08B 3/04; B08B 9/00
[52] U.S. Cl. .................................. 134/21; 134/22.12; 134/22.18; 134/24; 134/34; 422/33
[58] Field of Search .................. 134/21, 22.12, 22.18, 134/24, 166 C, 169 C, 171, 34; 128/6; 239/106, 112; 422/28, 33

[56] References Cited

U.S. PATENT DOCUMENTS 3,963,438  6/1976  Banez .

Primary Examiner—Marc L. Caroff

[57] ABSTRACT

In a method of cleaning an endoscope, a stop having a communication path is mounted on the open ends of an air/liquid supply valve cylinder and a suction valve cylinder of the endoscope so that liquid may flow between the valve cylinders through the communication path. One end of a suction channel, which opens to the distal end of an insertion section of the endoscope, is connected to a liquid tank through a liquid supply tube. An air supply pump is connected to the tank. The pump is operated in this state and supplies the liquid held in the tank to the one end of the suction channel. The liquid supplied to the one end of the suction channel is discharged from a nozzle at the distal end of the insertion section and the other ends of the suction channel, an air supply channel and a liquid supply channel, which open to a connector mounted on a light guide of the endoscope, through the three channels and the valve cylinders, thereby cleaning the interior of these channels and valve cylinders.

8 Claims, 5 Drawing Figures

METHOD OF CLEANING ENDOSCOPE CHANNELS

BACKGROUND OF THE INVENTION

The present invention relates to a method of cleaning various channels of an endoscope.

An endoscope generally has various channels for supplying or drawing by suction air or liquids. Therefore, when a used endoscope is to be cleaned, not only the outer surface thereof but also the channel interiors must be cleaned. The word "cleaning" used herein includes the steps of water cleaning for removing contaminants in the channels, disinfection with a disinfectant after such water washing, and then water washing after disinfection. These cleaning steps are usually performed in the order named above. However, in a conventional method of cleaning the channel interiors, a cleaning solution injection tube must be inserted in the port of each channel, and the valve of each channel must be opened. This requires connection of the cleaning solution injection tube into each channel and a switching operation of the valve of each channel. Procedures for cleaning channels of an endoscope have therefore been complex. With the conventional system as described above, there is an important problem in that incomplete cleaning frequently occurs, especially of the small portions of the valve body of the valve or the portion of the cylinder which is covered with the valve body.

In view of this problem, the present applicant has previously proposed, in Japanese Patent Application No. 56-111940, a cleaning instrument for cleaning channels of an endoscope which is free from such a problem. According to this instrument, the cleaning solution is supplied through an air/liquid supply cylinder and a suction cylinder formed in a control section of an endoscope so as to allow simultaneous cleaning of the interiors of the channels and the inner surfaces of the cylinders. More specifically, valve bodies inserted in the air/liquid supply cylinder and suction cylinder are pulled out, and adaptors are inserted in the open cylinders. Liquid supply tubes connected to these adaptors are connected to a liquid supply pump. A liquid is supplied from the liquid supply pump to the respective cylinders. The liquid is then flowed from the cylinders to the suction opening and nozzle at the distal end of the endoscope and to the air supply port, liquid supply port and suction port of the connector portion through the liquid supply channel, the air supply channel and the suction channel, respectively, thereby cleaning these channels.

However, the various channels of an endoscope generally have different inner diameters. More specifically, the air supply channel and liquid supply channel generally have small diameters while the suction channel has a large diameter. With one single channel alone, that portion of the channel which extends in the insertion section of the endoscope has a small diameter, and that portion of the channel which extends in the light guide cable has a large diameter. For this reason, when a liquid is supplied from the cylinders to the respective channels, the liquid flows to the channel or channel portion offering the least flow resistance, and a sufficient amount of cleaning solution cannot be flowed to a channel or channel portion offering a larger flow resistance. This results in a problem of incomplete cleaning of the endoscope channels.

SUMMARY OF THE INVENTION

Accordingly, the object of the present invention is to provide a method of cleaning channels of an endoscope, which makes it possible to easily and completely clean the channels and valve cylinders of an endoscope.

According to an aspect of the invention there is provided a method of cleaning the channels of an endoscope, which comprises a first step of mounting communicating means on the open ends of the air/liquid supply valve cylinder and suction valve cylinder so that liquid may flow between the valve cylinders; and a second step of supplying liquid from at least one of the following five ports and discharging the liquid from the remaining ports through the three channels, the air/liquid supply valve cylinder and the suction valve cylinder, thereby cleaning the interior of these channels and valve cylinders with the liquid:

(a) the nozzle;
(b) one end of the suction channel;
(c) the other end of the air supply channel;
(d) the other end of the liquid supply channel;
(e) the other end of the suction channel.

DETAILED DESCRIPTION OF THE PREFERRED EMBODIMENTS

A few preferred embodiment of the present invention will now be described with reference to the accompanying drawings.

Figure 1:
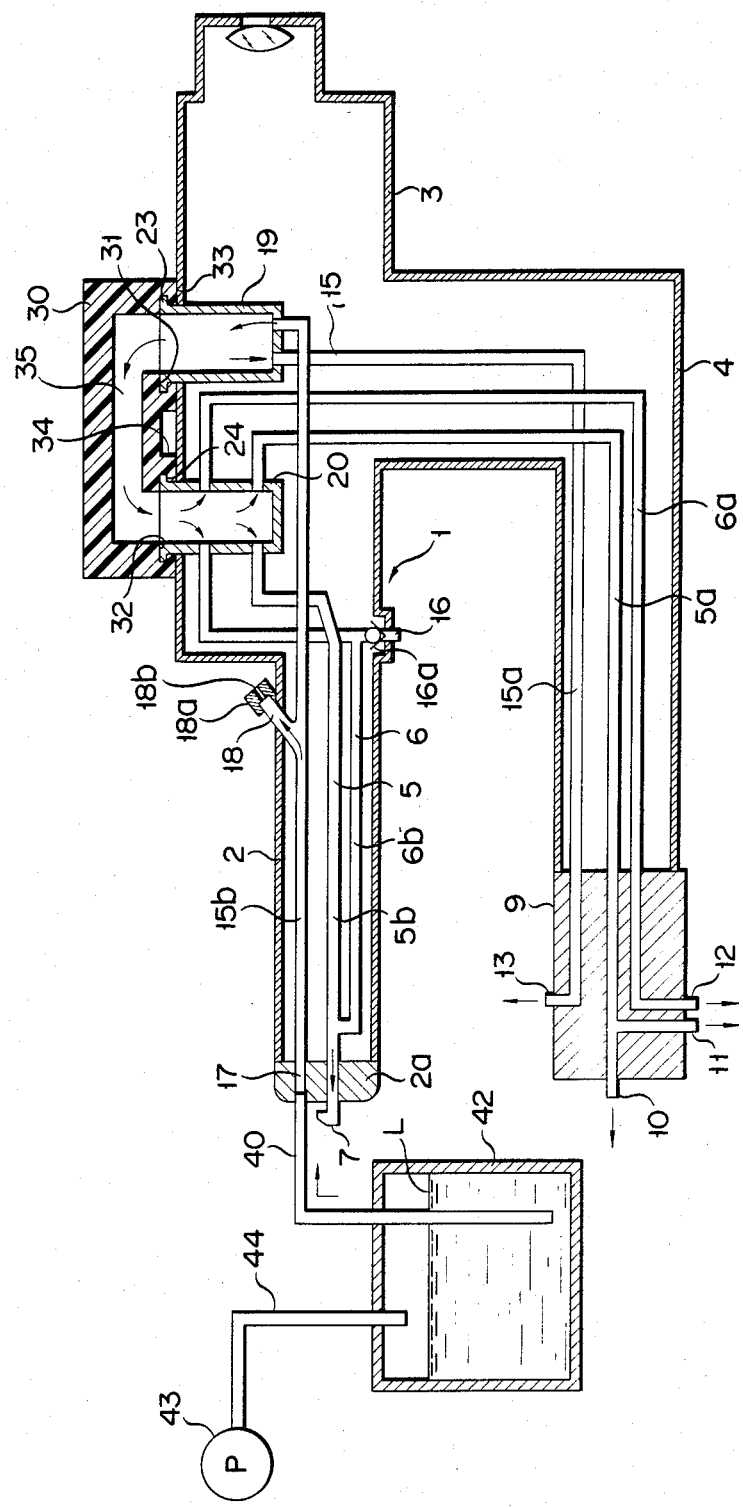
FIG. 1 is a cross-sectional view of an endoscope, showing how to clean channels by a first method according to the invention.

FIG. 1 is a cross-sectional view of an endoscope 1. The endoscope 1 comprises a control section 3, an insertion section 2 extending from the control section 2 and a light guide cable 4 extending from the control section 2. Various channels (described later) are formed inside the endoscope 1. First, an air supply channel 5 and a liquid supply channel 6 are formed extending through the insertion section 2, the control section 3 and the light guide cable 4. The distal ends of the air supply channel 5 and the liquid supply channel 6 merge to be connected to an air/liquid supply nozzle 7 at the distal end 2a of the insertion section 2. The air/liquid supply nozzle 7 is arranged to face the outer surface of an observation window (not shown) so as to spray air or a liquid thereagainst. The light guide cable 4 has a connector 9 at the free end. The connector 9 has first and second air supply ports 10 and 11 both communicating with the air supply channel 5, a liquid supply port 12 communicating with the liquid supply channel 6, and a suction port 13 communicating with a suction channel to be described later. When the connector 9 is connected to a light source device (not shown), the first air supply port 10 is connected to an air supply pump in the light source device. The second air supply port 11 and the liquid supply port 12 are connected to a liquid supply tank (not shown).

Meanwhile, a suction channel 15 is formed to extend along the entire length of the insertion section 2, the control section 3 and the light guide cable 4. That end portion of the suction channel 15 which is at the side of the insertion section 2 serves as an instrument insertion channel 15b. The distal end of the instrument insertion channel 15b communictes with a suction opening 17 opening to the distal end face of the insertion section 2. The proximal end of the instrument insertion channel 15b opens externally at the control section 3 to form a forceps port 18. The forceps port 18 is closed with a detachable stop 18a having a small hole 18b. A sub liquid port 16 having a check valve 16a communicates with the liquid supply channel 6.

The instrument insertion channel 15b is connected to the proximal end of the remaining portion, that is an upstream channel portion, of the suction channel 15 through a suction cylinder, that is, a suction valve cylinder 19. An air/liquid supply cylinder or air/liquid supply valve cylinder 20 is inserted midway along both the air supply channel 5 and the liquid supply channel 6. The valve cylinders 19 and 20 are arranged next to each other at a side surface of the control section 3. The upper ends of the valve cylinders 19 and 20 open to the outside of the control section 3. The suction valve cylinder 19 has a cylindrical shape with a bottom and has a flange 23 formed integrally therewith at its open edge or upper edge. The air/liquid supply valve cylinder 20 similarly has a cylindrical shape with a bottom and has a flange 24 formed integrally therewith at its open edge.

A stop 30 is mounted over the valve cylinders 19 and 20. The stop 30 has two mounting portions 33 and 34 having engagement grooves 31 and 32 formed in their inner circumferential surfaces for engagement with the flanges 23 and 24, respectively. Therefore, even if the internal pressure in the cylinders 19 and 20 is increased, the stop 30 may not be inadvertently removed. A communication path 35 is formed in the stop 30. When the stop 30 is placed over the valve cylinders 19 and 20, the interior of the valve cylinder 19 communicates with the interior of the valve cylinder 20 through the communication path 35. Pistons (not shown) are generally inserted in the cylinders 19 and 20. The pistons serve to allow or block communication between upstream channel portions 5a, 6a and 15a and downstream channel portions 5b, 6b and 15b of the channels 5, 6 and 15. When the stop 30 is to be mounted, the pistons are first removed.

Figure 2:
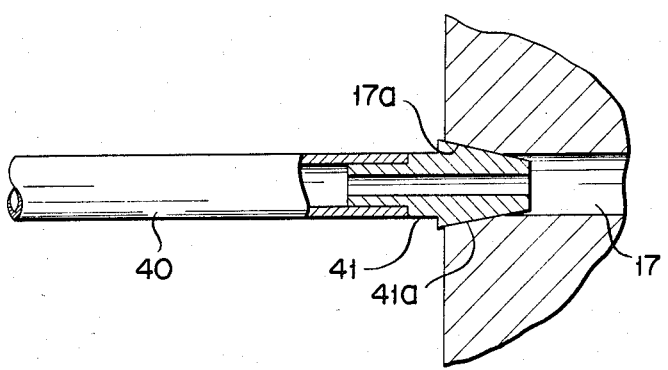
FIG. 2 is an enlarged sectional view showing a connecting state between a suction port and a liquid supply tube.

One end of a liquid supply tube 40 is liquid-tightly and detachably mounted through connecting port 41 at the suction opening 17 at the distal end 2a of the insertion section 2, as shown in FIG. 2. Tapered portions 41a and 17a for fitting the connecting port 41 and the suction port 17 together are formed therein. When these tapered portions 41a and 17a are fitted together, the connected state may not be released. The other end portion of the liquid supply tube 40 is hermetically inserted in a liquid tank 42, such that the tip of the other end of the tube 40 is submerged in a liquid L held therein. One end of an air supply tube 44 whose other end is connected to an air supply pump 43 is liquid-tightly inserted in the liquid tank 42. The open terminal end of the air supply tube 44 opens to the upper space within the liquid tank 42.

The method of cleaning the channels of the endoscope 1 described above will now be described. First, as shown in FIG. 1, the stop 30 is mounted over the cylinders 19 and 20, and the liquid supply tube 40 is connected to the suction opening 17. The stop 18a is mounted on the forceps port 18. When the air supply pump 43 is operated under these conditions, the interior of the liquid tank 42 is compressed by the air supplied from the air supply pump 43. Therefore, the liquid L is supplied therefrom along the liquid supply tube 40 and into the downstream channel portion 15b of the suction channel 15. The liquid L which has been supplied to the downstream channel portion 15b then flows into the suction valve cylinder 19 and thence into the air/liquid supply valve cylinder 20 through the communication path 35 of the stop 30. When the pressure of the liquid L in the cylinders 19 and 20 is increased to a predetermined level, the liquid L in the cylinder 19 flows into the upstream channel portion 15a of the suction channel 15 and then flows out from the suction port 13 of the connector 9. The liquid L in the air/liquid supply valve cylinder 20 flows into the upstream channel portions 5a and 6a and the downstream channel portions 5b and 6b of the air supply channel 5 and the liquid supply channel 6. The liquid L which has flowed into the upstream channel portions 5a and 6a flows out from the first and second liquid supply ports 10 and 11 and the liquid supply port 12. The liquid L which has flowed into the downstream channel portions 5b and 6b flows out from the air/liquid supply nozzle 7. Due to such flow of the liquid L, the channels 5, 6 and 15 can be cleaned along their entire length, and the cylinders 19 and 20 can be simultaneously cleaned. When the liquid L flows into the downstream channel portion 15b of the suction channel 15, some of this liquid flows out through the small hole 18b in the stop 18a mounted at the forceps port 18, and the interior of the forceps port 18 can thus be cleaned.

In the above description, the liquid is water or a disinfectant. In general, disinfection is performed with a disinfectant. However, the term cleaning used herein includes both washing with water and disinfection or sterilization.

According to the first embodiment, as has been described above, the air/liquid cylinder and suction cylinder are connected with each other through the communication path, so that liquid may flow between the cylinders. The liquid is supplied through the suction opening at the distal end of the insertion section, and the liquid flows out through the suction port, the air supply port and the liquid supply port at the connector portion and through the nozzle at the distal end of the insertion section. As a result, all the channels and cylinders of an endoscope can be easily cleaned. The liquid is supplied from an upstream channel portion of the suction channel having a diameter larger than that of the air or liquid supply channel so as to ensure a flow into the suction cylinder, and then the liquid flow is divided into a portion flowing into the downstream channel portion of the suction channel and a portion flowing into the air supply channel and liquid supply channel. Accordingly, even if the channels have different inner diameters, they can be cleaned along their entire length. Since the liquid is sprayed from the nozzle, any contaminates clogging the nozzle can be easily removed. The method of the above embodiment provides an excellent operability since all the channels of an endoscope can be simultaneously cleaned by supplying a liquid from on location.

In the first embodiment, the liquid supply tube 40 is connected to the suction opening 17 to supply the liquid into the suction channel 15. However, the liquid supply tube 40 may be connected to one of the other ports 10, 11, 12, 13, 16 or the nozzle 7.

Figure 3:
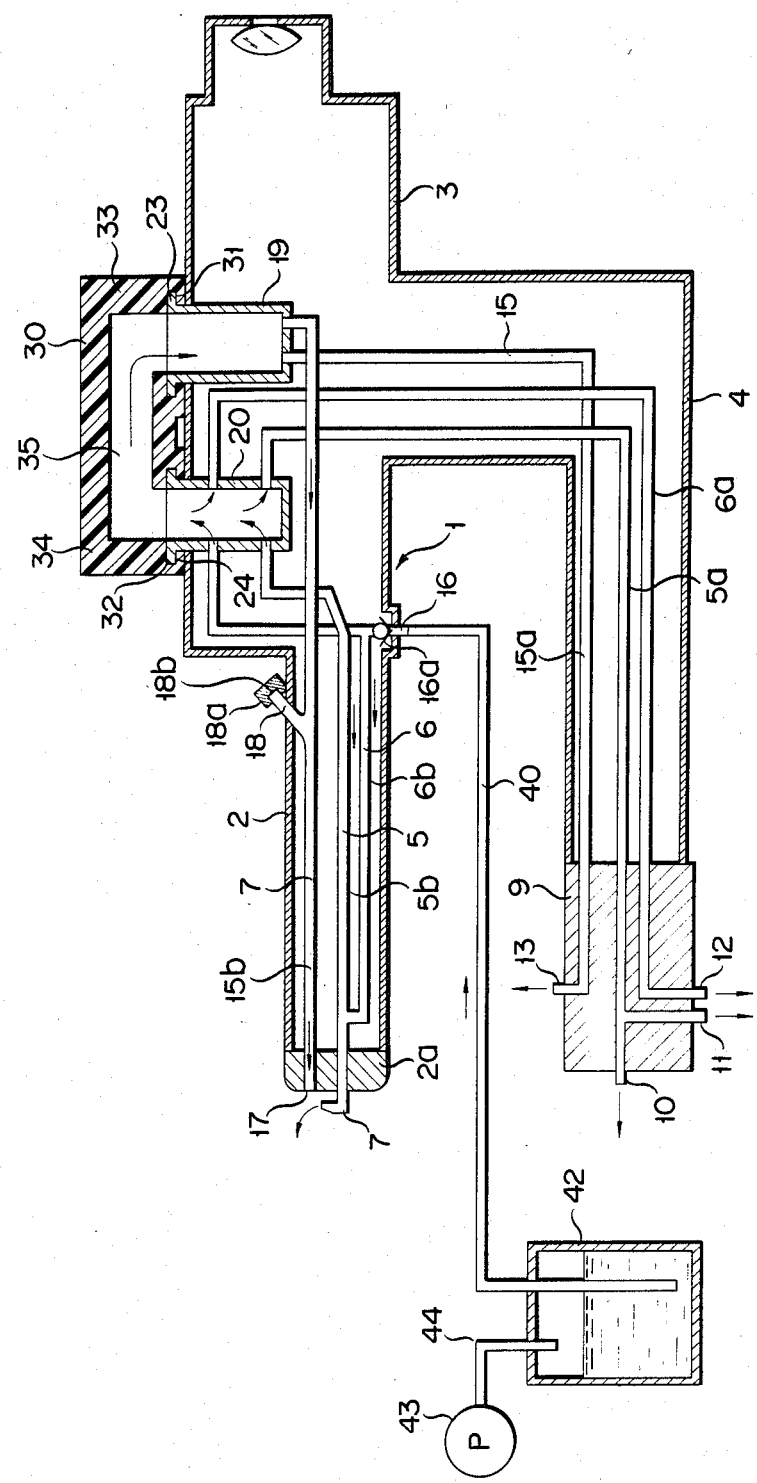
FIG. 3 is a cross-sectional view of the endoscope, showing how to clean the channels by a second method according to the invention.

In a second embodiment shown in FIG. 3, the liquid supply tube 40 is connected to the sub liquid supply port 16. In this case, when the air supply pump 31 is operated, the internal pressure in the liquid tank 42 is increased, and the liquid is supplied under pressure from the liquid supply tube 40 to the port 16. Then, the liquid flows into the downstream channel portion 6b of the liquid supply channel 6 from the sub liquid supply port 16. Part of the thus-supplied liquid is exhausted through the nozzle 7 at the distal end 2a of the insertion section 2, and the remainder flows into the air/liquid supply valve cylinder 20. The liquid which has flowed into the cylinder 20 is divided to flow into the upstream and downstream channel portions 5a and 5b of the air supply channel 5 and into the upstream channel portion 6a of the liquid supply channel 6. The liquid which has flowed into the downstream channel portion 5b is exhausted from the nozzle 7. The liquid which has flowed into the upstream channel portions 5a and 6a is exhausted from the first and second air supply ports 10 and 11 and the liquid supply port 12 of the connector 9. The liquid in the air/liquid supply valve cylinder 20 also flows into the suction valve cylinder 19 through the communication path 35 of the stop 30, and thereafter flows into the upstream and downstream channel portions 15a and 15b of the suction channel 15. The liquid which has flowed into the upstream channel portion 15a is exhausted from the suction port 13 of the connector 9, while the liquid which has flowed into the downstream channel portion 15b is exhausted through the suction opening 17 at the distal end 2a. Therefore, all the channels and cylinders of the endoscope 1 can be simultaneously cleaned, as in the first embodiment.

With an endoscope having a gas supply valve cylinder, the gas supply valve cylinder can be communicated with the other cylinders to allow simultaneous cleaning of all the channels.

Although the first and second embodiments are used in combination with the endoscope 1 which does not have a gas supply valve or a gas supply channel, the method of cleaning an endoscope according to the present invention can be similarly applied to an endoscope which has a gas supply valve and a gas supply channel. Also, in place of the air supply pump 43 and the liquid tank 42, a syringe can be used as liquid supply means for supplying liquid to an endoscope.

Figure 4:
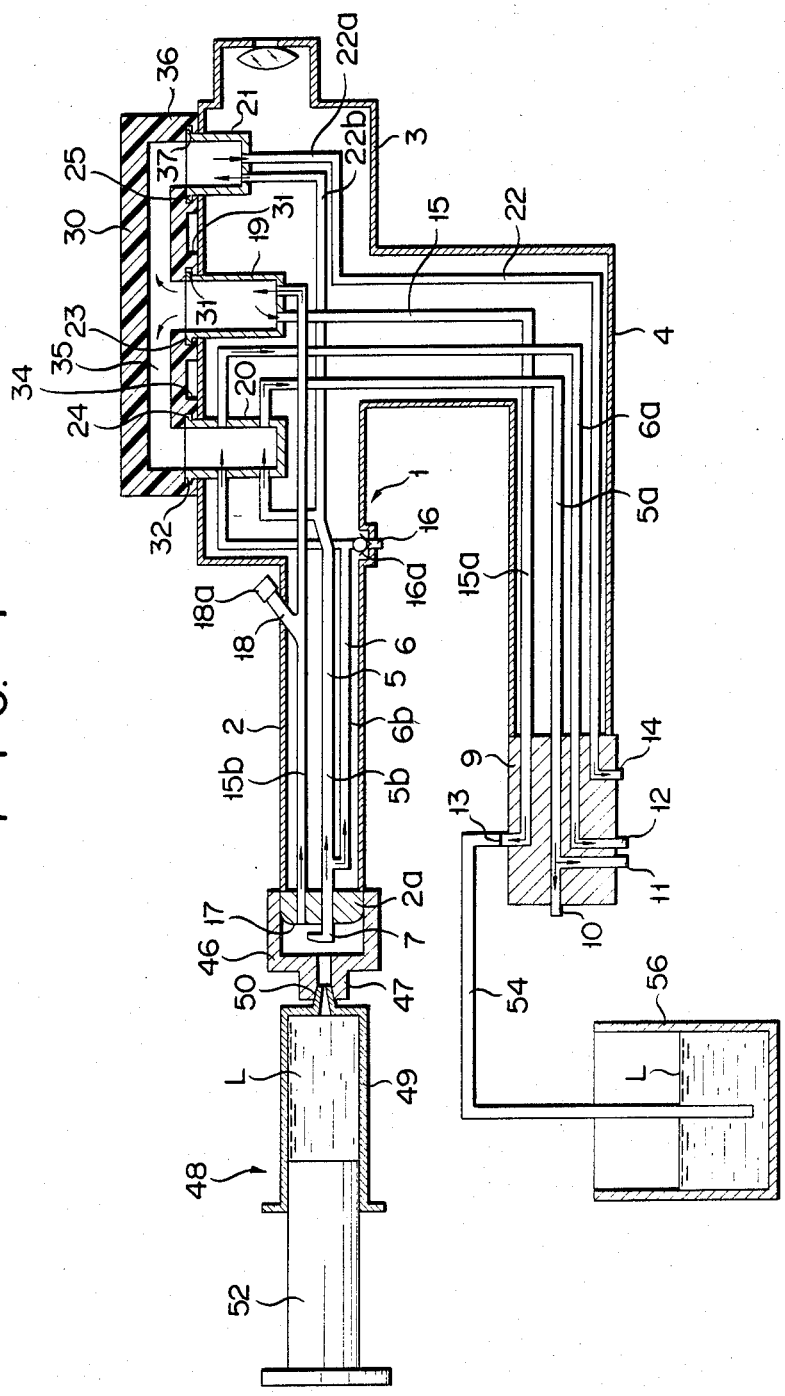
FIG. 4 is a cross-sectional view of another endoscope, showing how to clean channels by a third method according to the present invention.

FIG. 4 shows a third embodiment of the present invention. Of the members forming this embodiment, only those which are different from the members constituting the first embodiment will be described.

In the third embodiment, an endoscope 1 is provided with a gas supply valve cylinder 21 and a gas supply channel 22 connected to the cylinder 21. The gas supply valve cylinder 21 is arranged next to a suction cylinder 19 and its upper end opens to the outside of a control section 3. A flange 25 is formed integrally with the open edge of the cylinder 21. One end of the gas supply channel 22 is connected to the air supply channel 5 at a position between the air/liquid supply valve cylinder 20 and the nozzle 7. The other end of the gas supply channel 22 is connected to a gas supply port 14 which opens to a connector 9.

A stop 30 is mounted on the valve cylinders 19, 20 and 21. The stop 30 has three mounting portions 33, 34 and 36 which have in their inner circumferential surfaces engagement grooves 31, 32 and 37 for engagement with the flanges 23, 24 and 25. Therefore, even if the internal pressure of the cylinders 19, 20 and 21 is increased, the stop 30 may not be inadvertently removed. A communication path 35 is formed in the stop 30. When the stop 30 is placed over the valve cylinders 19, 20 and 21, the inner spaces of these valve cylinders communicate with one another through the communication path 35. Pistons (not shown) are generally inserted in the cylinders 19, 20 and 21. The pistons serve to allow or block communication of the channels 5, 6, 15 and 22. When the stop 30 is to be mounted, the pistons are first removed.

A liquid suction/exhaust cap 46 of an elastic material is detachably mounted at the distal end 2a of the insertion section 2. The liquid suction/exhaust cap 46 has a connecting portion 47 which is connected to a syringe 48. The syringe 48 has a cylinder 49 holding liquid L, a piston 52 slidably inserted in the cylinder, and a tapered connecting port 50 at the distal end of the cylinder. The connecting port 50 is detachably fitted to the connecting portion 47. One end of a liquid suction/exhaust tube 54 is connected to the suction port 13 of the connector 9, and the other end thereof is submerged in a liquid L held in a liquid tank 56.

Cleaning of various channels of the endoscope 1 will now be described. First, the stop 30 is mounted over the cylinders 19, 20 and 21. The syringe 48 holding the liquid L therein is connected to the distal end 2a of the insertion section 2 through the liquid suction/exhaust cap 46. The liquid suction/exhaust tube 54 is connected to the suction port 13 of the connector 9. When the piston 44 inserted in the cylinder 49 is pressed in this state, the liquid L flows as indicated by the arrows in the FIG. 4. More specifically, the liquid L in the cylinder 49 flows into the internal space of the liquid suction-/exhaust cap 46 and is supplied to downstream channel portions 5b and 6b of the air supply channel 5 and the liquid supply channel 6 and to a downstream channel portion 15b of the suction channel 15. The liquid L which has flowed under compression into the air supply channel 5 and the liquid supply channel 6 flows into the air/liquid supply valve cylinder 20. Part of the liquid L which has flowed into the air supply channel 5 passes along a downstream channel portion 22b of the gas supply channel 22 and flows into the gas supply valve cylinder 21. The liquid L which has been supplied to the suction channel 15 flows into the suction valve cylinder 19. The amount of liquid L which flows from the gas supply channel 22 to the gas supply valve cylinder 21 is small. However, a sufficient amount of the liquid L flows into the gas supply valve cylinder 21 from the suction valve cylinder 19 and the air/liquid supply valve cylinder 20 through the communication path 35 of the stop 30. When the pressure of the liquid L in the cylinders 19, 20 and 21 and the communication path 35 is increased considerably, the liquid L flows into the upstream channel portions 5a, 6a, 15a and 22a of the channels 5, 6, 15 and 22, respectively. Then, the liquid L which has flowed into the upstream channel portion 5a of the air supply channel 5 flows out from the first and second air supply ports 10 and 11 of the connector 9. The liquid L which has flowed into the upstream channel portion 6a of the liquid supply channel 6 flows out from the liquid supply port 12. The liquid L which has flowed into the upstream channel portion 22a of the gas supply channel 22 flows out from the gas supply port 14. The liquid L which has flowed into the upstream channel portion 15a of the suction channel 15 flows into the liquid tank 56 from the suction port 13 through the liquid suction/exhaust tube 54.

After supplying the liquid L under pressure to the channels 5, 6, 15 and 22, the piston 52 inserted in the cylinder 49 is pulled in the opposite direction out of the cylinder 49. Then, the interior of the cylinder 49 is kept at a negative pressure, and therefore the channels 5, 6, 15 and 22 communicating with the syringe 48 are also kept at a negative pressure. Then, the liquid L flows in the opposite directions to those indicated by the arrows. Thus, the liquid L remaining in the channels 5, 6, 15 and 22 is drawn into the syringe 48, and the liquid L in the liquid tank 56 is also drawn into the syringe 48 through the liquid suction/exhaust tube 54 and the suction channel 15. Therefore, when the above operation, that is, pushing in and pulling out of the piston 52 inserted in the cylinder 49, is repeated several times, the channels 5, 6, 15 and 22 are cleaned along their entire length. At the same time, the cylinders 19, 20 and 21 are also cleaned.

Figure 5:
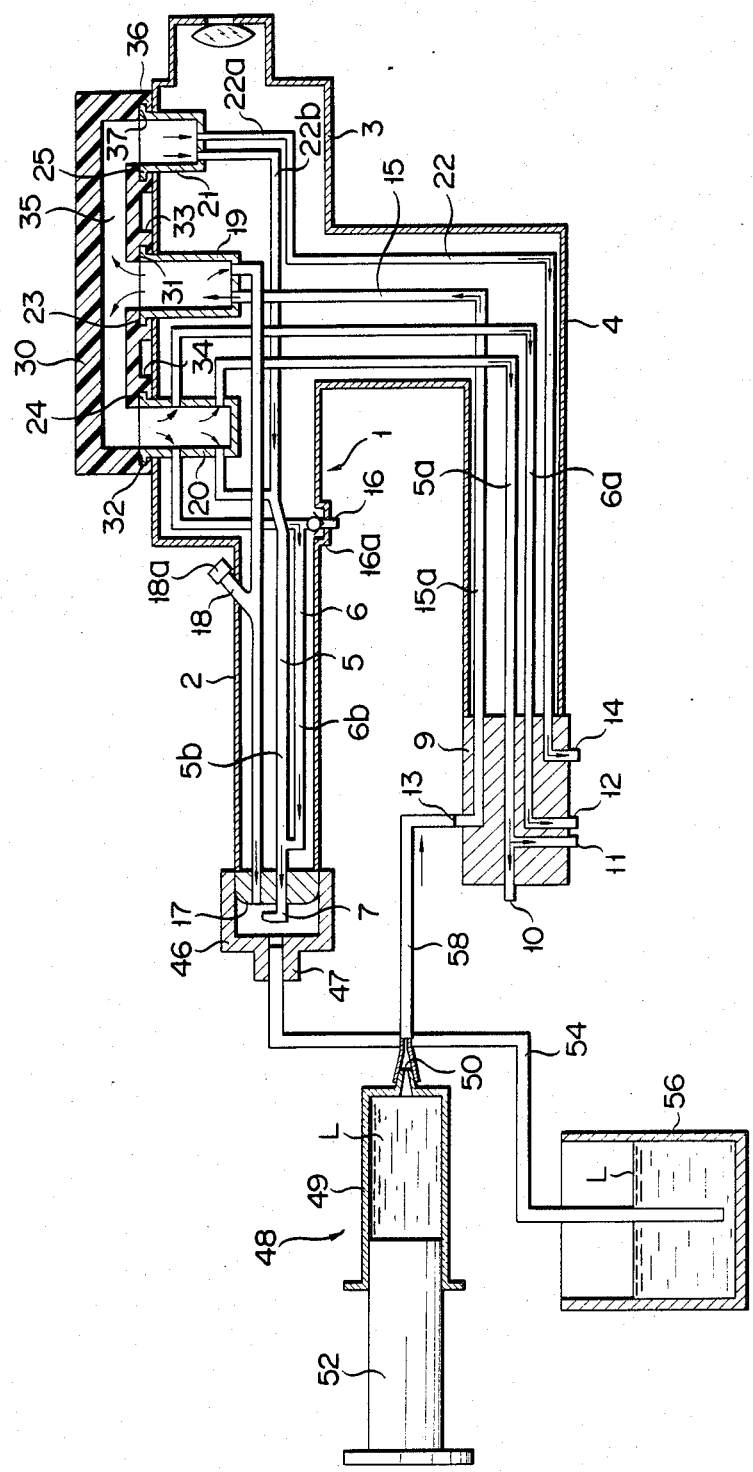
FIG. 5 is a cross-sectional view of the endoscope shown in FIG. 4, illustrating how to clean the channels by a fourth method according to the invention.

FIG. 5 shows another embodiment of the present invention. In this embodiment, the syringe 48 is connected to the suction port 13 of the connector 9 through a second liquid suction/exhaust tube 58. One end of the liquid suction/exhaust tube 54 the other end of which is submerged in the liquid L held in the liquid supply tank 56 is connected to the liquid suction/exhaust cap 46.

When the piston 52 inserted in the cylinder 49 is pressed, the liquid L flows in the direction indicated by the arrows in the FIG. 5. When the piston 52 is pulled in the opposite direction, the liquid L is drawn in the opposite directions to those indicated by the arrows and flows into the cylinder 49. When the piston 52 inserted in the cylinder 49 is pressed, the liquid L flows from the upstream channel portion 15a of the suction channel portion 15 into the suction valve cylinder 19. Part of the liquid L which has flowed into the cylinder 19 flows along the downstream channel portion 15b of the suction channel 15 and then out from the suction opening 17 into the liquid tank 56. The liquid L which has flowed into the cylinder 19 flows into the air/liquid supply valve cylinder 20 and the gas supply valve cylinder 21 through the communication path 35 of the stop 30. The liquid L which has flowed into the air/liquid supply valve cylinder 20 flows into the upstream channel portions 5a and 6a and the downstream channel portions 5b and 6b of the air supply channel 5 and the liquid supply channel 6. The liquid L which has flowed into the upstream channel portions 5a and 6a flows out from the first and second air supply ports 10 and 11 and the liquid supply port 12. The liquid L which has flowed into the downstream channel portions 5b and 6b flows out from the nozzle 7 and into the liquid tank 56. The liquid L which has flowed into the gas supply valve cylinder 21 flows into the upstream and downstream channel portions 22a and 22b. The liquid L then flows out from the gas supply port 14 through the upstream channel portion 22a, and also flows out from the nozzle 7 through the downstream channel portion 22b to be recovered into the liquid tank 56.

When the piston 52 is pulled out to place the cylinder 49 at a negative pressure, the liquid L flows in the opposite directions to those indicated by the arrows. The liquid L in the liquid tank 56 is also drawn into the syringe 48.

In the fourth embodiment, as in the case of the third embodiment described above, the channels 5, 6, 15 and 22 can be cleaned along their entire length while at the same time the cylinders 19, 20 and 21 are also cleaned.

In the embodiments shown in FIGS. 4 and 5, a check valve can be connected to each of the first and second air supply ports 10 and 11, the liquid supply port 12 and the gas supply port 14 in a direction such as to allow only the outward flow of the liquid from the connector 9 from the corresponding channels. Thus, when the piston 52 inserted in the cylinder 49 is pulled out, external air may not be drawn into the endoscope through the ports 10, 11, 12 and 14. Therefore, when the interior of the cylinder 49 of the syringe 48 is kept at a negative pressure, a large amount of the liquid L in the liquid tank 56, that is, of a relatively clean liquid L which has not yet been used for cleaning, is drawn into the syringe 48. When the piston 52 is subsequently pushed into the cylinder 49, the liquid L is flowed out therefrom to clean the channels 5, 6, 15 and 22 and the cylinders 19, 20 and 21.

In the third and fourth embodiments described above, if the liquid L exhausted from the liquid suction/exhaust tube 54 upon pressing of the piston 52 is not recovered into the liquid tank 56 but is exhausted externally, the liquid L in the liquid tank never becomes contaminated. If a small hole is formed in the stop 18a mounted at the forceps port 18 to allow outward flow of the liquid L through this small hole in a small amount, the forceps port 18 can be reliably cleaned.

The means for forcibly supplying and drawing by suction a liquid is not limited to the syringe 48 but can be a pump or the like.

What is claimed is:

1. A method of cleaning an endoscope which includes a control section, an insertion section extending from the control section and having a nozzle at its distal end, a light guide cable extending from the control section and having a connector at its distal end, an air supply channel extending in the endoscope and having one end communciating with the nozzle and the other end opening to the connector, a liquid supply channel extending in the endoscope and having one end communicating with the nozzle and the other end opening to the connector, a suction channel extending in the endoscope and having one end opening to the distal end of the insertion section and the other end opening to the connector, an air/liquid supply valve cylinder arranged in the control section to communicate with the air supply channel and liquid supply channel and having one end opening to the outside of the control section, and a suction valve cylinder arranged in the control section to communicate with the suction channel and having one end opening to the outside of the control section; said method comprising:

a first step of mounting communicating means on the open ends of the air/liquid supply valve cylinder and suction valve cylinder, so that liquid is confined to flow between the valve cylinders, and a second step of supplying liquid from at least one of the following five ports and discharging the liquid from the remaining ports through the three channels, the air/liquid supply valve cylinder and the suction valve cylinder, thereby cleaning the interior of the channels and valve cylinders with the liquid:
(a) the nozzle;
(b) said one end of the suction channel;
(c) the other end of the air supply channel;
(d) the other end of the liquid supply channel;
(e) the other end of the suction channel.

2. A method according to claim 1, wherein said liquid is supplied from said one end of the suction channel to the endoscope.

3. A method according to claim 1, wherein said endoscope has a sub liquid port communicating with the liquid supply channel, and said liquid is supplied from at least one of said six ports to the endoscope.

4. A method according to claim 3, wherein said liquid is supplied from the sub liquid port and is discharged from said nozzle and the remaining four ports.

5. A method according to claim 1, wherein said liquid is supplied from the nozzle and said one end of said suction channel into the endoscope and is discharged from the other ends of the three channels.

6. A method according to claim 1, wherein said second step includes connecting a liquid tank filled with liquid to at least one of said five ports through a liquid supply tube and pressurizing the liquid in the liquid tank to supply the liquid into the liquid supply tube.

7. A method according to claim 1, which further comprises a third step of bringing at least one of the remaining ports into contact with liquid, and a fourth step of sucking the liquid from at least one of said five ports through the three channels, the air/liquid supply valve and the suction valve cylinder.

8. A method according to claim 1, wherein said endoscope has a gas supply channel extending in the endoscope and having one end communicating with the air supply channel at a position between the air/liquid supply valve cylinder and the nozzle and the other end opening to the connector, and a gas supply valve cylinder arranged in the control section to communicate with the gas supply channel and having one end opening to the outside of the control section; said first step includes mounting said communication means on the open end of the gas supply channel so that liquid is confined to flow between the three valve cylinders; and said liquid is supplied from at least one of said five ports and discharged from the remaining ports through the four channels and three cylinders.

* * * * *